(12) United States Patent
Andersson et al.

(10) Patent No.: US 10,744,217 B2
(45) Date of Patent: Aug. 18, 2020

(54) DEVICE AND METHOD FOR WASHING, DISINFECTING AND/OR STERILIZING

(71) Applicant: GETINGE STERILIZATION AB, Getinge (SE)

(72) Inventors: Jonas Andersson, Halmstad (SE); Per Norlin, Torslanda (SE)

(73) Assignee: GETINGE STERILIZATION AB, Getinge (SE)

( * ) Notice: Subject to any disclaimer, the term of this patent is extended or adjusted under 35 U.S.C. 154(b) by 0 days.

(21) Appl. No.: 15/026,440

(22) PCT Filed: Oct. 3, 2013

(86) PCT No.: PCT/EP2013/070628
§ 371 (c)(1),
(2) Date: Mar. 31, 2016

(87) PCT Pub. No.: WO2015/049002
PCT Pub. Date: Apr. 9, 2015

(65) Prior Publication Data
US 2016/0235879 A1   Aug. 18, 2016

(51) Int. Cl.
*A61L 2/24*   (2006.01)
*G06F 21/31*   (2013.01)

(52) U.S. Cl.
CPC ............... *A61L 2/24* (2013.01); *G06F 21/31* (2013.01); *A61L 2202/14* (2013.01); *A61L 2202/24* (2013.01)

(58) Field of Classification Search
CPC ................... A61L 2/24; G06F 21/31
See application file for complete search history.

(56) References Cited

U.S. PATENT DOCUMENTS 6,522,939 B1 *   2/2003   Strauch ............ G05B 19/41875
                                                    700/116
7,138,087 B1 *   11/2006  Malkin .................. A61B 1/123
                                                    422/1
(Continued)

FOREIGN PATENT DOCUMENTS

CN    1918567 A    2/2007
CN    101219072 A   7/2008
(Continued)

OTHER PUBLICATIONS

International Search Report for Application No. PCT/EP2013/070628 dated Jan. 23, 2014.
(Continued)

*Primary Examiner* — Regina M Yoo

(57) ABSTRACT

A device a method, and a computer program for use in a device (40) for washing, disinfecting and/or sterilizing medical, dental, laboratory and/or pharmaceutical goods. The device comprises a chamber (41) for receiving the goods, a door (42) associated with the chamber (41) and a processing circuitry for creating and storing a track record of at least one parameter of the washing, disinfecting and/or sterilizing process performed by the device (40). The user interface (44, 45) is operable by the user to cause the process circuitry to electronically sign the track record, and wherein the signing of the track record is associated with at least one condition on the device (40). The device, method and computer program facilitates an easy and secure signing of a track record directly on the device.

21 Claims, 4 Drawing Sheets

(56) References Cited

U.S. PATENT DOCUMENTS

| | | | | |
|---|---|---|---|---|
| 2003/0206826 | A1* | 11/2003 | Stanley | A01N 37/16 422/28 |
| 2004/0091389 | A1* | 5/2004 | Malkin | A61B 1/123 422/26 |
| 2005/0109070 | A1 | 5/2005 | Kobayashi et al. | |
| 2006/0251540 | A1* | 11/2006 | Benning | A61L 2/24 422/3 |
| 2007/0202005 | A1 | 8/2007 | Maschke | |
| 2009/0308758 | A1* | 12/2009 | Kim | A61L 12/023 205/464 |
| 2010/0282135 | A1 | 11/2010 | Ko | |
| 2011/0027123 | A1* | 2/2011 | Dings | A61L 12/04 422/1 |
| 2012/0282135 | A1 | 11/2012 | Trapani | |
| 2014/0037495 | A1* | 2/2014 | Ahiska | A61L 2/24 422/3 |

FOREIGN PATENT DOCUMENTS

| | | |
|---|---|---|
| CN | 101605565 A | 12/2009 |
| EP | 1882479 A1 | 1/2008 |
| JP | 2010-119491 A | 6/2010 |
| WO | 8604698 A1 | 8/1986 |
| WO | 2005004931 A1 | 1/2005 |
| WO | 2007021696 A2 | 2/2007 |
| WO | 2012/092445 A2 | 7/2012 |

OTHER PUBLICATIONS

International Preliminary Report on Patentability for Application No. PCT/EP2013/070628 dated Feb. 11, 2016.

English translation of Japanese Office Action dated Nov. 14, 2017 for corresponding Japanese Patent Application No. 2016-546148, 3 pages.

EP Office Action dated Apr. 24, 2018 which issued for corresponding EP Patent Application No. 13774390.2, 4 pages.

Chinese Office Action and Search Report (with English translations of same) dated Apr. 24, 2018 for corresponding Chinese patent application No. 201380080079.7, 13 pages.

Final Office Action dated Nov. 27, 2018 which issued for U.S. Appl. No. 15/026,894, filed Apr. 1, 2016, 11 pages.

Operator Manual Basil 9500 Cage and Rack Washer, Jan. 20, 2006, 98 pages.

Tuttnauer Operation & Maintenance Manual, Cat. No. MAN205-0112003EN Rev. N, 57 pages (date unknown).

Webpage printout: https://www.allclaveparts.com/tuttnauer-troubleshooting/tuttnauer-automatic-autoclaves/tuttnauer-autoclave-error-codes-display-messages, 2018, 7 pages. Is purported evidence that Tuttnauer autoclave has been available since at least 2011, per top of p. 7. Applicant takes no position regarding art dates for autoclave or manual.

Brazilian Office Action dated May 22, 2019 which issued for corresponding Brazilian Patent Application No. BR112016007383-5, 4 pages.

* cited by examiner

DEVICE AND METHOD FOR WASHING, DISINFECTING AND/OR STERILIZING

CROSS-REFERENCE TO RELATED APPLICATION

This application is a national phase entry under 35 U.S.C. § 371 of International Application No. PCT/EP2013/070628, filed on Oct. 3, 2013, the disclosure of which is incorporated herein by reference.

TECHNICAL FIELD

A device and a method for washing, disinfecting and/or sterilizing medical, dental, laboratory and/or pharmaceutical goods. The device is adapted to permit a user to electronically sign a track record created by the device, and optionally to store the signed track record on the device.

BACKGROUND OF THE INVENTION

The pharmaceutical industry, hospitals, care centers, laboratories and similar industries and facilities are constantly struggling against contaminations such as bacterial infections and viral infections. Hygiene issues are constantly on the topic and continuously evaluated. One hygiene issue of special character is the washing, disinfecting and sterilization of goods, such as sterilizing medical, dental, laboratory and/or pharmaceutical goods. The goods may be reusable goods or disposable goods.

Reusable goods used on such facilities can be surgical equipment such as knifes, graspers, clamps, retractors, dilators, probes, scopes, drills, and saws, laboratory equipment such as bottles, bowls, condensers, funnels, flasks, pipettes and plates, or the like. Any object which is intended to be reused and which can be contaminated with hazardous or biological substances is the subject of harsh hygiene conditions. Whenever reusable goods have been used, such as reusable medical equipment, the reusable goods are sent for washing, disinfecting and/or sterilization.

The process of washing, disinfecting and sterilizing goods, such as reusable medical equipment mentioned above, is a very high demanding process in terms of the rules and regulations, facilities used, the staff, the process parameters, the apparatuses and even the ambient environment surrounding the apparatuses. All restrictions and conditions serving the purpose to reduce, or eliminate, the risk for contamination makes it difficult and costly to operate washing, disinfecting and/or sterilizing processes.

For example, a pharmaceutical production site may be equipped with steam generators, water pretreatment apparatuses, Closure processing systems, discharge systems, component washers, glassware washers, component sterilizer, terminal sterilization systems, isolators and sterility testing equipment, simply to clean and sterilize different reusable medical equipment. The cleaning and the sterilizing apparatuses are further usually separated in different environmental zones, each environmental zone having its own environmental conditions imposed thereon. Such environmental conditions can be demands on humidity, temperature, air pressure, ventilation systems, and access to clean water, or the like.

Examples of different environmental areas, or zones, in which the environmental conditions can vary are distribution areas, reception areas, clean areas and sterile areas. Each area is generally separated by a zone barrier. A zone barrier can be a physical wall which is keeping an air pressure differential, and can sometimes be referred to as a cross-contamination wall. A cross-contamination wall can be air sealed and adapted to physically prevent staff members from moving between the environmental areas and air to travel there between. All precautionary measures are thus taken to prevent cross contamination between the environmental areas.

Some cleaning devices, such as sterilizers for example, may be of a pass-through model. A pass-through sterilizer extends across a zone barrier and permits a staff member to load goods at one end of the sterilizer and unload sterilized goods at the other end. The sterilizer thus extends across at least one zone barrier.

The harsh hygiene conditions imposed on each environmental area, the zone barriers between the environmental areas, and the limited freedom of movement between the environmental areas for the staff members, impose high demands on the apparatuses and washing, disinfection and sterilization processes used therein.

To secure that the goods is properly treated, cleaned, disinfected or sterilized, the staff member may be required to check the track record, also referred to as batch or process record. Track records are recorded by separate computers or printers and are inspected using a graph in analog or in digital form. The staff member usually also has to make an ocular inspection of the goods to secure that the goods is in good condition and not for example wet or damaged. When these inspections have been successfully carried out, the staff member prints out a track record and sign it. The track record is thereafter put in a folder and filed. However, there is nothing that stops the staff member from releasing the sterilized goods earlier before these inspections have been carried out.

There is a possibility that due to human mistakes the goods can be unloaded and released from the sterilizer without being formally approved. If the sterilized goods are not inspected there is a risk that errors or faults in the sterilization process are not discovered. Furthermore, if a formal approval is missing, it is a clear indication that the inspection has not been successfully or appropriately carried out. This could have severe consequences causing non sterile or contaminated medical, dental, laboratory and/or pharmaceutical goods to be released.

There is thus a need to simplify the formal approving process of a batch before releasing the batch from the sterilizer. There is also a need to improve the sterilizing apparatus to prevent non sterile medical, dental, laboratory and/or pharmaceutical goods to be accidentally or incorrectly released.

SUMMARY

It is an object of the present invention to provide for a device and a method which removes, or at least reduces the above mentioned drawbacks, or which provides a useful alternative to known prior art. The object is at least partly met by a device for washing, disinfecting and/or sterilizing medical, dental, laboratory and/or pharmaceutical goods using a washing, disinfecting and/or sterilizing process. The device comprises a chamber for receiving the medical, dental, laboratory and/or pharmaceutical goods, at least one user interface permitting a user to operate the device and a door associated with the chamber. The device further comprises a processing circuitry for creating a track record of at least one parameter of the washing, disinfecting and/or sterilizing process performed by the device. The user interface is operable by the user to cause the process circuitry to electronically sign the track record, and wherein the signing of the track record is associated with at least one condition on the device.

By imposing at least one condition on the device, a procedure is established which enforces that the sequencing of batch approval and an imposed condition, such as physical release of the medical, dental, laboratory and/or pharmaceutical goods is maintained. It is a very cost effective solution compared to using separate systems. It is a robust system which automatically generates an electronic track record which can be stored by the device, e.g. a washer, disinfector, autoclave, sterilizer, itself. It can reduce the dependence on communication with separate systems for signature and record creation. Furthermore, it removes the need for print outs and storage, and separate tracking system of paper copies.

The present invention is based on a belief that the procedure, and device, for quality securing that the medical, dental, laboratory and/or pharmaceutical goods has been properly washed, disinfected and/or sterilized may include the steps of; inspection, approval, release and/or generation of an electronically signed track record optionally in combination with an audit trail. Each of the steps can be conditioned. The condition can further be suppressed, activated, and/ or revealed, by the electronic signing of the track record.

According to an aspect, the condition is imposed on the door of the device. This condition is related to the release of the medical, dental, laboratory and/or pharmaceutical goods. A condition imposed on the door of the device can be permitting the opening and/or permitting closing of the door of the device. For example as the user has signed the track record on the user interface, the device unlocks the door, permitting a user to open the door and unload the medical, dental, laboratory and/or pharmaceutical goods loaded in the device. A condition, in addition or optionally, can be that the door is opened or closed by the device itself.

According to an aspect, a check list can be displayed on the user interface, preferably after or before the washing, disinfecting and/or sterilizing process is initiated or completed. The check list can be interactive so that the user can "tick" when a point on the check list is performed or checked. When the check list is completed, e.g. the door of the device can be opened or permitted to be opened so that the good can be loaded or released. The check list can be a standard check list or a customised check list, e.g. customised by the user. The check list can be displayed before or after the signing is performed.

According to an aspect, The device has two doors one for loading goods from a non sterile or a contaminated side and one door used to unload the cleaned or sterilized goods. The door in the loading side cannot be opened before the door on the unloading side has been opened and closed indicating that the processed goods has been removed. If an one door solution is used to bout load and unload the goods it is up to the user to secure that the track record is properly signed.

According to an aspect, the at least one user interface is integrated with the device, optionally the user interface can comprise a mobile unit, such as a touch pad, mobile smart phone or the like. The at least one user interface can comprise a touch-sensitive display for signing the track record. It is advantageous if the signed track record is stored locally, at least as a backup.

According to an aspect, the signing of the track record is irreversible. It is important that when a user has signed the track record, the signed track record cannot be manipulated or changed afterwards. At least the identity of the signer and/or date of approval should not be able to be removed or manipulated from the track record, so that traceability and audit of stored track records are not only possible, but can be performed without the risk of signed track records being accidentally or intentionally manipulated.

According to an aspect, the at least one parameter of the process is temperature, pressure, time, volume such as washing liquid volume, rinsing water volume, concentrations, pH, media quality, ions in the washing water (hardness), consumables such as detergents, salt, or the like. One or more parameters for creating a track record can be selected.

The track record can of course include an audit trail comprising identification and time and date of important events. Both the audit trail and the other selected one or more parameters are thus electronically signed.

According to an aspect, the device is a sterilizing device. The process is in this case a sterilizing process. The device can also be a high level disinfection device, the process being a high level disinfection (HLD) process for the reprocessing of semi-critical devices, including flexible endoscopes, or for sterilization of critical or semi-critical devices that are 30 heat-sensitive or incompatible with traditional sterilization methods. Endoscope reprocessing, for instance, involves the cleaning and disinfection of endoscopes, and may encompass the steps of cleaning, rinsing, disinfection, secondary rinsing, drying and storing. For drying, a drying cabinet is commonly utilized, which drying cabinet may comprise a door, a cabinet, a control circuit and a loading system such as one or several shelves or hooks. Use of the drying cabinet enables for immediate reuse of e.g. endoscopes, even after extended storage periods thereof. Drying cabinets may comprises the invention as described herein.

The present invention also relates to a method for electronically signing a track record of a process for washing, disinfecting and/or sterilizing medical, dental, laboratory and/or pharmaceutical goods performed by a device. The device comprises a chamber for receiving the medical, dental, laboratory and/or pharmaceutical goods, at least one user interface to operate the device, at least one door associated with the chamber, and a processing circuitry for creating a track record of at least one parameter of the process performed by the device. The method comprises;

registering at least one parameter of the process;
forming a track record based on the registration;
electronically signing the track record via the user interface;
imposing a condition on the device based on the electronically signing of the track record.

By imposing at least one condition on the device and associate that condition with the signing of the track record which is equivalent with a user accepting or acknowledging that the medical, dental, laboratory and/or pharmaceutical goods has been washed, disinfected and/or sterilized in an acceptable manner or to an acceptable level of pureness, a procedure is established which enforces that the sequencing of batch approval and an imposed condition, such as physical release of the medical, dental, laboratory and/or pharmaceutical goods, is maintained.

The method can be manipulated so that an electronic track record is automatically generated for the user to be signed. The signed track record can thereafter be stored by the device, e.g. on an autoclave/sterilizer, itself. The method reduces the dependence on communication with separate systems for signature and record creation. Furthermore, it removes the need for print outs and storage of paper copies.

According to an aspect, the condition is associated with the door of the device. The method can thus include the step of; opening the door of the device after the electronically signing the track record via the user interface is performed, or permitting the door to be opened after the electronically signing the track record via the user interface is performed.

The method can additionally or optionally include the step of; closing the door of the device after the electronically signing the track record via the user interface is performed, or permitting the door to be closed after the electronically signing the track record via the user interface is performed. This step will prevent any user from starting the device until the track record has been signed, as the door to the chamber cannot be closed until the signing is complete. In an embodiment, a new process cannot be started before the track record of the previous process has been formally approved, or disapproved, by signing the display of the device. This is especially valuable for one door systems where there are limited means to ensure that the user signs the track record before proceeding and release the goods.

According to an aspect, the method is disinfection or sterilizing process performed by the device. The device can be a dedicated sterilizing device.

According to an aspect, the present invention relates to a computer program product for use in a device for washing, disinfecting and/or sterilizing medical, dental, laboratory and/or pharmaceutical goods. The device comprises a chamber for receiving the medical, dental, laboratory and/or pharmaceutical goods, at least one user interface permitting a user to operate the device, at least one door associated with the chamber, a processing circuitry for creating a track record of at least one parameter of the washing, disinfecting and/or sterilizing process performed by the device. The computer program product comprises code instructions configured for execution by the processing circuitry and which code instructions when executed in the device causes the device to permit a user via the user interface to electronically sign the track record, and associate the signing of the track record with at least one condition on the device.

The computer program product can be in the form of a data carrier carrying computer program code for performing the embodiments herein when being loaded into the device. One such carrier may be in the form of a CD ROM disc, a memory stick, a server or other suitable carriers or medium. The computer program code may furthermore be provided as a program code on a server and downloaded to the device, and executable on the device. The device may further comprise a memory comprising one or more memory units.

Generally, it is possible that at least one signature is required. In an embodiment two or more signatures are required to sign the track record to impose the condition on the device. The signatures may be by the same person or it may be required that two unique persons sign. It is also possible that the condition imposed on the device is that an additional signing is required.

BRIEF DESCRIPTION OF THE DRAWINGS

Non-limiting embodiments of the present invention will be described in greater detail with reference to the accompanying figures in which.

DETAILED DESCRIPTION OF PREFERRED EMBODIMENTS

Figure 1:
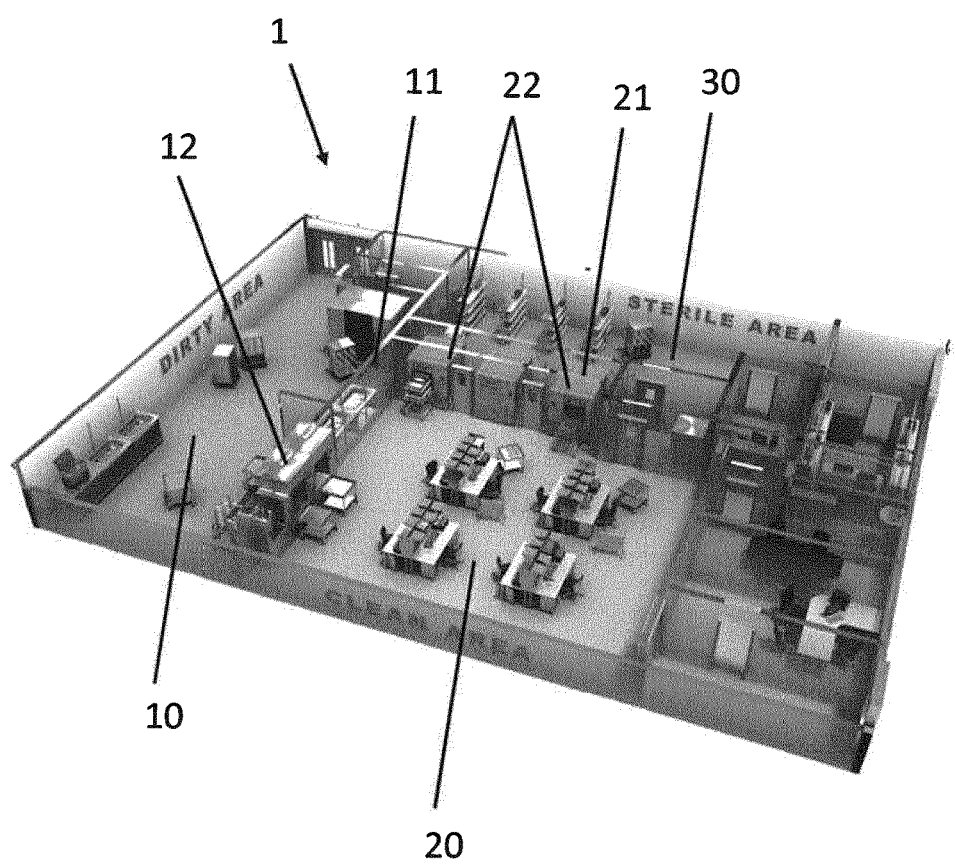
FIG. 1 shows a schematic illustration of a facility for washing, disinfecting and sterilizing medical, dental, laboratory and/or pharmaceutical goods.

FIG. 1 shows a schematic view in perspective of a facility 1 adapted for cleaning, washing, disinfecting and/or sterilizing medical equipment but the invention is applicable to medical, dental, laboratory and/or pharmaceutical goods for, or used in, Bio-Pharmaceutical Production, Medical Device Production, Bio-Medical Research and Laboratories, Hospitals (Sterile processing departments & Wards), Outsourced sterilization, Clinics & Practice (i.e. Dentists) and/or Elderly care.

The facility 1 has in the shown embodiment different environmental areas each serving its own specific purpose. The facility 1 comprises a dirty or contaminated area 10, a clean area 20, and a sterile area 30. Each area is separated by a zone barrier adapted to restrict access between the environmental areas.

The dirty area 10 is adapted to receive goods, in this case used medical equipment such as knifes, graspers, clamps, retractors and the like, which is in the need of cleaning, washing, disinfection and/or sterilization. The dirty area 10 is in the shown case also a reception area for the used medical equipment. A first zone barrier 11, in the form of a cross contamination wall, separates the dirty area 10 from the clean area 20. As can be seen, the first zone barrier 11 restricts all staff members from direct access between the dirty area 10 and the clean area 20 to prevent accidental contamination between the areas.

A washer 12 to clean the used medical equipment is arranged in the zone barrier 11. The washer 12 is of a pass through model, permitting staff members to load the washer 11 in the dirty area 10, and staff members to unload the washer in the clean area 20 after the used medical equipment has been washed. The used medical equipment is now deemed to be cleaned and thus referred to as clean medical equipment.

When a staff member unloads the washed and disinfected equipment in the clean area 20, the staff member, hereafter referred to as the user, might want to control and document that the cleaning process has been performed correctly. This is done visually and by studying a track record of the cleaning process. The track record can comprise information such as time, and temperature curves water consumption or similar, so that the user can confirm that the cleaning process has been performed correctly. When reprocessing the medical devices that cannot be sterilized due to material composition, material incompatibility with the sterilization process or heat sensitiveness it is advantageous if the compliance with the reprocessing method is ensured. The user can electronically sign the track record directly on the washer 12 so that the medical equipment can be unloaded and released to the next station. The electronic signing, the device and method used, will be described in greater detail below.

In the clean area 20, the clean medical equipment is arranged and prepared for further treatment. The clean medical equipment can be sorted and packed in air tight bags for example. A second zone barrier 21 separates the clean area 20 from the sterile area 30. Pass through models of autoclaves, in this case steam sterilizers, are arranged to extend across the second zone barrier 21 for further treatment of the clean medical equipment. Examples of further treatment of the clean medical equipment can be kill (effluent) cycles for pathogenic waste decontamination, wellbalanced processes for open liquids to minimize loss of the product liquid, adaptation to required BSL level or other specific applications. In general the treatment is performed at high temperatures using steam (but not all).

After the clean medical equipment has been sterilized it can be referred to as sterile medical equipment. The sterile medical equipment can now be released and is ready to be transported to a storage room at the facility and is ready to be used again.

When a staff member unloads the sterile medical equipment in the sterilized area 30, the staff member, hereafter referred to as the user, will need to control and document that the sterilization process has been performed correctly. This is done visually and by studying a track record of the sterilization process. The track record can comprise information such as time, temperature and pressure curves or similar, so that the user can confirm that the sterilizing process has been performed correctly.

Figure 2:
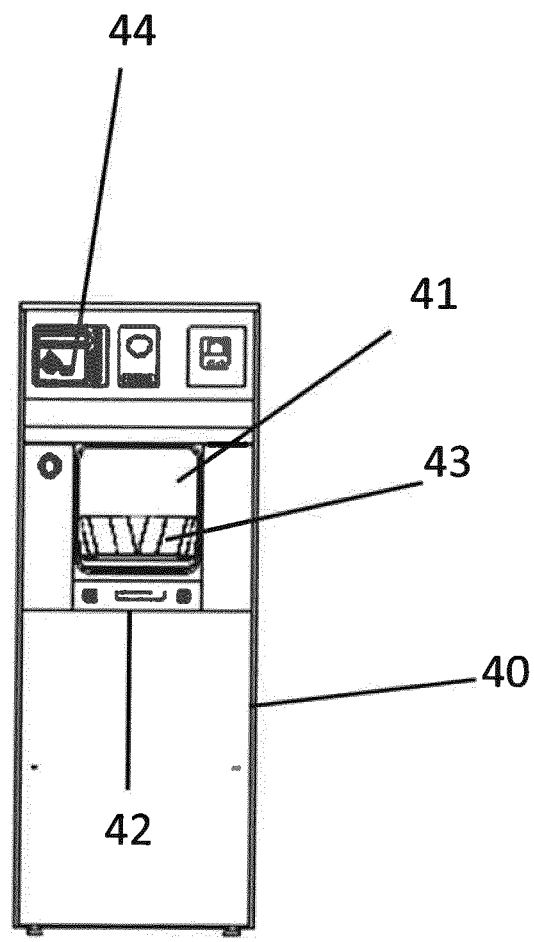
FIG. 2 shows a sterilizing device.

FIG. 2 shows a steam sterilizer 40, hereafter referred to as the sterilizer 40, in greater detail. The sterilizer 40 can be of a one door type or of a pass through model, having doors on opposite sides of the sterilizer permitting the sterilizer 40 to bridge across a zone barrier, such as a cross contamination wall 11, 21. The sterilizer comprises a chamber 41 for receiving the medical equipment for sterilization. A slideable door 42 is adapted to seal the chamber 41. A tray 43 is configured to receive the medical goods inside of the chamber. The tray is removable from the chamber 41. A user interface 44 is adapted so that the user can operate the sterilizer 40, in the shown embodiment a touch sensitive display is used as a user interface.

Sterilization (or sterilisation) herein relates to a process that eliminates, removes or kills microbial life, including transmissible agents (such as fungi, bacteria, viruses, spore forms, etc.) present on a surface, contained in a fluid, in medication, and/or on and/or in a compound such as biological culture media. Sterilization can be achieved by applying heat, chemicals, irradiation, high pressure, and filtration or combinations thereof.

Steam sterilization, or autoclaving, involves subjecting goods to steam at a high temperature. Steam sterilization involves the use of saturated steam under pressure and is a non-toxic method for sterilization. Further, steam sterilizers (autoclaves) are available in different sizes for different purposes.

Four factors are relevant for the outcome of steam sterilization: steam, pressure, temperature and time. The device 40 for washing, disinfecting and/or sterilizing medical, dental, laboratory and/or pharmaceutical goods using a washing, disinfecting and/or sterilizing process, should preferably be adapted to operate at a temperature above 100° C., preferably above 120° C., more preferably between 120-140° C. and at suitable pressure, at least above 101,3 kPa, or corresponding pressure for saturated steam. A sterilizer disclosed herein should preferably at least meet the requirement of EN285:2006 and A2:2009, standards used in this field of technology and known to the skilled person in the art.

The sterilisation time required varies depending on the goods to be sterilised, sterilisation time necessary at a defined temperature will also depend on the goods to be sterilised. Chemical and biological indicators are available for monitoring the sterilisation process and to ensure that sterility is achieved. Properly executed steam sterilisation will inactivate all fungi, bacteria, viruses and bacterial spores. If not all fungi, bacteria, viruses and bacterial spores can be inactivated, the temperature, time and pressure is selected so that the sterilization device, and the method, has a Sterility assurance level, SAL, of at most $1/1.000.000$, preferably lower than $1/1.000.000$. SAL is used to describe the probability of a non sterile unit exiting the device or method after the sterilization process has been completed.

The sterilizer 40 comprises a process circuitry (not shown) for creating a digital track record of the sterilizing process. The track record is made by registering at least one parameter of the sterilizing process such as temperature, pressure, time, volume such as washing liquid volume, rinsing water volume, or the like. The registering can be done by means of recording measurements of the at least one parameter, which are stored locally or remotely. If stored remotely, the sterilizers 40 comprises a communication unit adapted to forward the track record, or parts thereof, to the remote storage device. By locally is meant that the rack record is stored in the sterilizing device itself on a storage device such as hard drive or similar.

A sterilizing process is generally including but not limited to the steps of; loading the medical, dental, laboratory and/or pharmaceutical goods to be sterilized, choosing a sterilizing program, performing the sterilizing process, unloading the sterilized medical, dental, laboratory and/or pharmaceutical goods. Somewhere after the sterilizing process is completed, or partly completed, the user may want to inspect that the sterilizing process has been performed correctly. The inspection can be made by visually viewing a temperature/time graph tracking the steam temperature during the sterilization process, or by viewing a computer generated parameter(s), value(s) or graph(s), associated with the registered track record. In case of a graph, the graph can be plotted directly on the user interface, in this case the touch sensitive display 44. The user can thereafter acknowledge that the track record has been controlled and accepted. The acknowledgement is performed by electronically signing the track record, e.g. digitally signing the track record.

The electronically signing of the track record can be done using a personal and/or group identification sign. Examples of a personal identification sign are identification signs which are unique for one individual while a group identification sign can be used by a limited number of people e.g. 2-20 users. In the latter case the group of people is generally authorized to sign the track record. Examples of identification signs are personal codes such as identification numbers, names, passwords or similar, finger prints, voice recognition, eye reticule identification, or the like.

Figure 3:
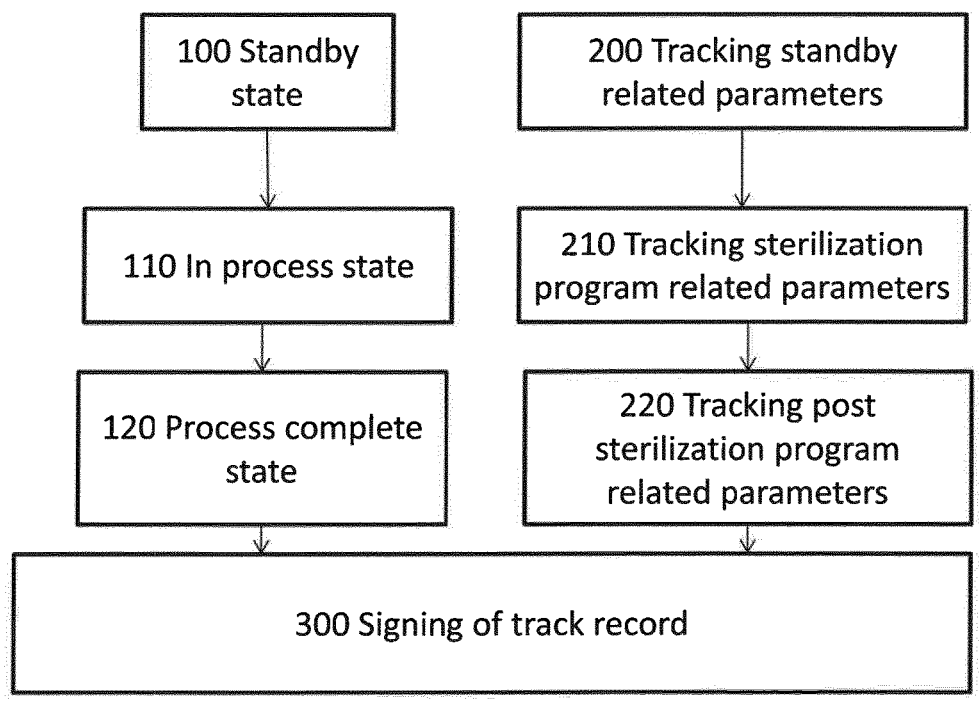
FIG. 3 shows a process flow for a sterilizing device and the flow for tracked parameters.

FIG. 3 shows a schematic diagram of a sterilizing process comprising the three distinct states, FIG. 3 shows; a stand by state 100, an in process state 110 and; a process complete state 120. Please notice that the sterilization process can comprise additional steps other than those described herein.

With reference to FIGS. 2 and 3; with the stand by state 100, the user is free to load a batch of the sterilizing device 40 with the medical, dental, laboratory and/or pharmaceutical goods to be sterilized. An appropriate sterilization program is selected on the program selection menu displayed on the user interface 44, in this case a touch screen 45. When the appropriate program is selected, the graphical interactive user-interface object representing a start button is activated on the touch screen so that the user can start the sterilization program. Hence a graphical interactive user-interface object which is relevant for the current state of the sterilizing process is displayed, while at least one graphical interactive user-interface object not relevant for the current state is inactivated. A user is now free to start the sterilization program. As an alternative, the program to select and start can be controlled by a separate device such as an automatic loading system or similar.

After the sterilization program has been initiated, the sterilization device 40 is in process state 110. In this state the sterilization device 40 initiates and performs the sterilization program to sterilize the medical, dental, laboratory and/or pharmaceutical goods in the chamber 41. In this state, the user interface displays the remaining time of the sterilization program and the only graphical interactive user-interface object which is activated for use is a cancel function. Exceptions may be for graphical interactive user-interface objects which are not related to the sterilizing process, such as general menu buttons.

When the sterilizing device 40 has finished the sterilization program, the sterilization device 40 enters the process complete state 120. In the process complete state, the user may open the door 42 to access the chamber 41 of the sterilizing device 40.

The process circuitry is adapted to register different parameters during the sterilization process. For example, during the standby state 100, the process circuitry can register stand by related parameters 200 such as the weight or position of the medical, dental, laboratory and/or pharmaceutical goods loaded in the chamber 41 of the sterilization device 40, the current temperature or status of a heating element for the steam generator, the time elapsed since the last sterilization program was performed, or similar.

During the in process state 110, the process circuitry can register sterilization program related parameters 210 such as temperature, pressure, time, incoming media quality, or the like. The registration is performed using at least one sensor. The sensors and how to register each parameter are known per se and will not be discussed further herein. Examples of other parameters are volume such as washing liquid volume, rinsing water volume, consumables such as detergents, pH, salt concentration.

In the process complete state 120, the process circuitry can register post sterilization program related parameters such as if the door is opened or closed, medical, dental, laboratory and/or pharmaceutical goods is unloaded, measuring time from when the program is finished or the like.

When the track record is created or subsequently after, the user is invited to electronically sign the track record 300.

Figure 4:
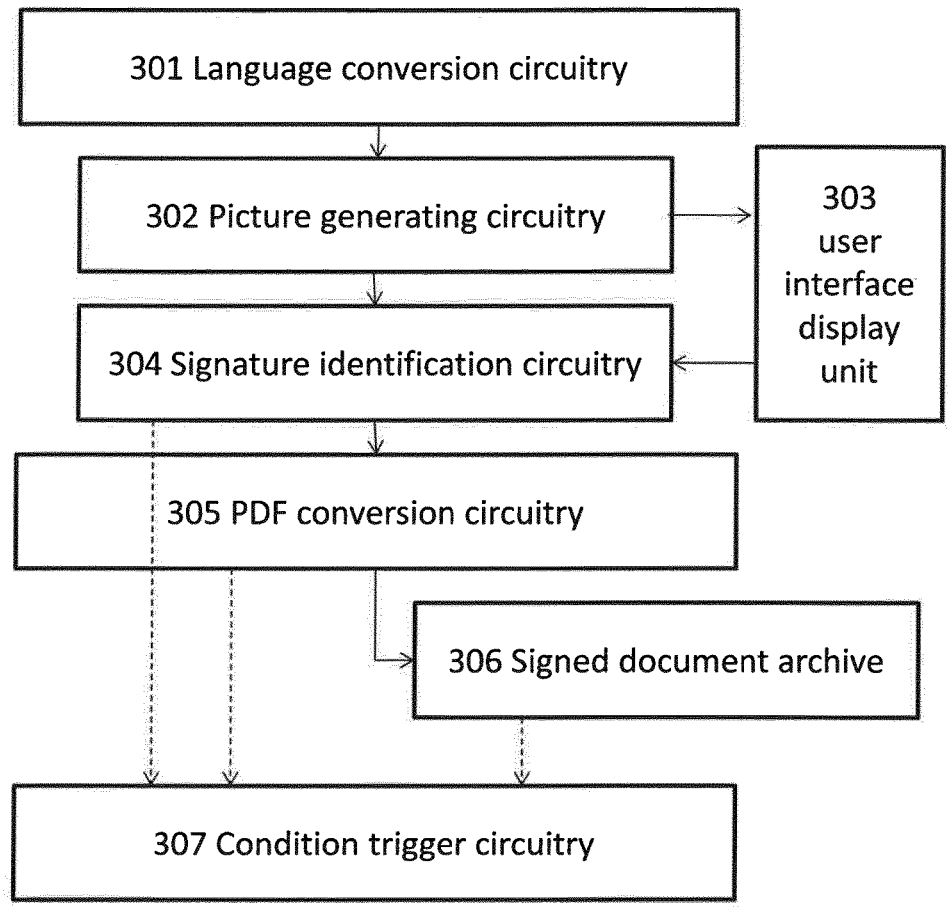
FIG. 4 shows a process flow for electronically signing of the track record.

FIG. 4 shows a non-limiting embodiment of how the box 300 (FIG. 3) can be configured. As mentioned, the sterilizing device 40 is adapted to permit a user to electronically sign the track record using the user interface of the sterilizing device 40.

A language conversion circuitry 301 converts the registered data into an acceptance format data for picture conversion. A picture generating circuitry 302 is used to convert the acceptance format data into a picture. The picture is displayed on a user interface display unit 303. The user interface display unit 303 is the user interface 44, in this case the touch screen 45 shown in FIG. 2. The user can sign his or hers name directly on the user interface display unit 303. Optionally the user interface display unit 303 displays a graphical interactive user-interface object or, such as an alphanumeric pad or similar, permitting the user to enter credentials as for example a code and an user ID to confirm who approved that the sterilization program has been performed in an acceptable manner. If an alphanumeric pad is used, the user could enter one or several codes representative for the identity of the user and an approval of the process.

A signature identification circuitry 304 identifies the signature and thus the identity of the user who signs the user interface display unit 303. The identification can be made by comparison with locally stored data or with remotely stored data.

The PDF conversion circuitry 305 converts the signed acceptance format data into a PDF file or other similar tamper proof format. A tamper proof electronically signed file of the track record is now formed. The tamper proof electronically signed file of the track record can be stored locally on a hard drive or remotely in a cloud or on a server. The tamper proof electronically signed file of the track record can be stored together with additional information such as the date and time, identification information of the medical, dental, laboratory and/or pharmaceutical goods which has been sterilized, batch number, and optionally at least one more parameter such as the selected sterilization program, or the like. Optionally such additional information is included in the track record and is thus signed together with the track record.

Optionally the user can use voice recognition for signing the track record, other methods of electronically signing is also possible.

The signing of the track record triggers at least one condition 307. The condition can be triggered when the signature identification circuitry 304 has identified the identity of the user, when the PDF conversion is complete, or when the signed track record is archived, i.e. stored, for example.

With reference to FIG. 2, the at least one condition can be that the user is enabled to open or close the door 42 to the chamber 41, or it can be that the sterilization device 40 open or close the door 42 to the chamber 41. In a preferred embodiment, the condition is associated with the door 42 of the chamber 41 of the sterilization device, preventing a user to open or close the door 42 to the chamber 41. It could optionally or additionally be that the user interface display unit is prevented from other input data until the signing is complete.

The imposed condition with the signing of the track record will prevent a batch of medical, dental, laboratory and/or pharmaceutical goods from being released without a user controlling that the sterilization program has been performed in a predetermined manner, or in an acceptable manner. In an embodiment, this is done by preventing the door 42 from being opened before the track record of the sterilization process is signed by the user. In another embodiment the sterilization device 40 is prevented from being loaded with new medical, dental, laboratory and/or pharmaceutical goods to be sterilized before the track record of the sterilization process has been signed by preventing the door 42 from being closed. If a two door system is used the unloading door could be prevented from being closed until the track record is signed. With the unloading door being open the loading door cannot be opened prohibiting new goods being loaded in to the machine and a new process started.

After the signature has been done, the signed document cannot be manipulated in the sense that the signing of the track record is irreversible, preferably for everybody, but at least for the user identified through the signature.

Other conditions are possible in combination or alone, to prevent the goods, in this case the medical equipment, from being unloaded from the device, or released from the specific area, to ensure that insufficiently washed, disinfected or sterilized goods, or contaminated goods, accidentally leaves the sterile area 30.

Optionally, or additionally, the device is tamper proof in terms of that only authorized staff has access to, and is permitted to use, the device. Optionally or additionally, all regulated data is maintained, can be reconstructed and can be readily retrieved. Optionally or additionally, the uniqueness of authentications (e.g., User ID and Password combinations) regarding using the device and applying electronic signatures can be guaranteed.

Optionally or additionally, electronic signatures cannot be removed, copied/pasted to other electronic records or otherwise tampered with.

The invention claimed is:

1. A device for washing, disinfecting and/or sterilizing medical, dental, laboratory and/or pharmaceutical goods using a washing, disinfecting and/or sterilizing process, said device comprising:
   a chamber inside the device for receiving the medical, dental, laboratory and/or pharmaceutical goods;
   a door on the device associated with the chamber;
   at least one user interface configured to permit a user to operate the device; and
   processing circuitry configured to execute code instructions, to record measurements of at least one parameter of the washing, disinfecting and/or sterilizing process performed by the device, and to create a digital track record of the washing, disinfecting and/or sterilizing process;
   wherein the at least one user interface is operable by the user to review and accept the digital track record after the washing, disinfecting, and/or sterilizing process has been completed;
   wherein the processing circuitry is programmed so that after the washing, disinfecting, and/or sterilizing process has been completed, an acceptance of the digital track record results in at least one of: opening the door, closing the door, allowing opening of the door, and allowing closing of the door; and
   wherein the device is one of: an autoclave for steam sterilization, a drying cabinet, a washer, and a chemical sterilizer.

2. The device according to claim 1, wherein the at least one user interface is operable by a user to apply an electronic signature to the digital track record to accept the digital track record; and
   wherein the electronic signature comprises a personal and/or group identification sign.

3. The device according to claim 1,
   wherein the processing circuitry is further programmed to prohibit a subsequent second washing, disinfecting and/or sterilizing process until the an electronic signature is applied.

4. The device according to claim 1, wherein the at least one parameter of the washing, disinfecting and/or sterilizing process is chosen from a group including temperature, pressure, time, washing liquid volume, rinsing water volume, quantity of detergent, pH, and/or salt concentration.

5. The device according to claim 1:
   wherein the processing circuitry is programmed to perform further steps including:
      displaying a checklist comprising a plurality of checklist items to be performed or checked; and
      after the washing, disinfecting, and/or sterilizing process has been completed, permitting the door to open and/or to close in response to a user indicating that each of the plurality of checklist items have been respectively performed and/or checked.

6. The device according to claim 1:
   wherein the device comprises an autoclave for steam sterilization.

7. The device according to claim 1:
   wherein the device is a pass through device comprising two doors associated with the chamber, including a first door for receiving medical, dental, laboratory, and/or pharmaceutical goods, and a second door for removal of said medical, dental, laboratory, and/or pharmaceutical goods after a washing, disinfecting, and/or sterilizing process has been completed;
   the processing circuitry being further programmed wherein after said washing, disinfecting and/or sterilizing process is completed, and when the second door is in an open state: the second door is prevented from closing until a user accepts the digital track record.

8. The device according to claim 1:
   wherein the device is a pass through device comprising two doors associated with the chamber, including a first door for receiving medical, dental, laboratory, and/or pharmaceutical goods, and a second door for removal of said medical, dental, laboratory, and/or pharmaceutical goods after said washing, disinfecting, and/or sterilizing process has been completed; and
   wherein the device extends through a cross-contamination wall, and the first door and the second door are positioned on opposite sides of the cross-contamination wall.

9. A device for washing, disinfecting and/or sterilizing medical, dental, laboratory and/or pharmaceutical goods using a washing, disinfecting and/or sterilizing process, said device comprising:
   a chamber for receiving said medical, dental, laboratory and/or pharmaceutical goods; the chamber being located within the device;
   at least one user interface configured to permit a user to operate said device;
   a door associated with said chamber, the door being on a surface of the device;
   processing circuitry configured to create a digital track record, the digital track record including at least one parameter of said washing, disinfecting and/or sterilizing process performed by said device;
   a data carrier holding code instructions, the code instructions being configured for execution by the processing circuitry;
   wherein the processing circuitry is programmed to perform steps including:
      creating the digital track record for the washing, disinfecting and/or sterilizing process; then
      after the digital track record has been created, and after the corresponding washing, disinfecting and/or sterilizing process has been completed: receiving an electronic signature from a user via the at least one user interface for the digital track record, the electronic signature including a personal and/or group identification sign and indicating acceptance of the digital track record; and
      in response to receiving the electronic signature, the electronic signature being for the digital track record, at least one of: opening the door, closing the door, allowing opening of the door, and allowing closing of the door.

10. The device according to claim 9,
    wherein the device comprises two doors positioned for accessing the chamber, including a first door for receiving medical, dental, laboratory, and/or pharmaceutical goods, and a second door for removal of said medical, dental, laboratory, and/or pharmaceutical goods after said a washing, disinfecting, and/or sterilizing process has been completed;

wherein the processing circuitry is further programmed to perform further steps including:

after the washing, disinfecting and/or sterilizing process is completed, and when the second door is in an open state: preventing closing of the second door until the electronic signature is received.

11. The device according to claim 9:

wherein the device comprises two doors positioned for accessing the chamber, including a first door for receiving medical, dental, laboratory, and/or pharmaceutical goods, and a second door for removal of said medical, dental, laboratory, and/or pharmaceutical goods after said a washing, disinfecting, and/or sterilizing process has been completed;

wherein the processing circuitry is further programmed to perform further steps including:

after the washing, disinfecting and/or sterilizing process is completed, and when the second door is in an open state and the first door is in a closed state: preventing closing of the second door until the electronic signature is received, and preventing opening of the first door until the second door has been closed.

12. The device according to claim 9:

wherein the device is a pass through device comprising two doors associated with the chamber.

13. The device according to claim 1, wherein the device is one of: an autoclave for steam sterilization, a drying cabinet, a washer, and a chemical sterilizer.

14. The device according to claim 9, wherein said at least one user interface is comprised in a mobile unit.

15. The device according to claim 9, wherein said at least one user interface comprises a touch-sensitive display configured for applying the electronic signature to said digital track record.

16. The device according to claim 9, wherein said electronic signature is irreversible.

17. The device according to claim 9, wherein said at least one parameter of said washing, disinfecting and/or sterilizing process is selected from a list of: temperature, pressure, time, washing liquid volume, pH, salt concentration, and rinsing water volume.

18. The device according to claim 1, wherein said electronic signature indicates approval by the user of the digital track record for said washing, disinfecting, and/or sterilizing process; and wherein the processing circuitry is further programmed to prohibit a subsequent second washing, disinfecting and/or sterilizing process until the electronic signature is applied.

19. The device according to claim 1, wherein said device is one of: an autoclave for steam sterilization, a drying cabinet, and a washer.

20. A pass through device for washing, disinfecting and/or sterilizing medical, dental, laboratory and/or pharmaceutical goods using a washing, disinfecting and/or sterilizing process, said pass through device comprising:

a chamber inside the pass through device for receiving said medical, dental, laboratory and/or pharmaceutical goods;

a user interface;

two doors on the pass through device and associated with said chamber, including a loading door and an unloading door;

processing circuitry, the processing circuitry configured for creating a digital track record including at least one parameter of said washing, disinfecting and/or sterilizing process; and a data carrier holding code instructions;

wherein the processing circuitry is programmed to perform steps including:

creating the digital track record;

after the washing, disinfecting and/or sterilizing process has been completed: receiving an electronic signature from a user via the user interface for the digital track record; and after the washing, disinfecting and/or sterilizing process has been completed, preventing the unloading door from being closed until the electronic signature is received.

21. The pass through device according to claim 20:

wherein the processing circuitry is further programmed so that when the unloading door is in an open state and the loading door is in a closed state: the loading door is prevented from opening until the unloading door is closed.

* * * * *